(12) United States Patent
Roxendal et al.

(10) Patent No.: US 6,245,961 B1
(45) Date of Patent: Jun. 12, 2001

(54) ABSORBENT ARTICLE

(75) Inventors: Sofia Roxendal, Pixbo; Peter Rönnberg; Roy Hansson, both of Mölndal, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/328,456

(22) Filed: Jun. 9, 1999

(30) Foreign Application Priority Data

Dec. 3, 1997 (SE) .................................................. 9704484
Jul. 6, 1998 (SE) .................................................. 9802427

(51) Int. Cl.[7] ...................................................... A61F 13/15
(52) U.S. Cl. .......................... 604/367; 604/380; 604/378; 604/384
(58) Field of Search .................................... 604/367, 358, 604/365, 378–384, 368–377

(56) References Cited

U.S. PATENT DOCUMENTS

| | | |
|---|---|---|
| 3,371,667 | 3/1968 | Morse . |
| 4,129,132 * | 12/1978 | Butterworth et al. . |
| 4,360,022 | 11/1982 | Usami et al. . |
| 4,781,710 * | 11/1988 | Megiaon et al. ...................... 604/378 |
| 5,368,909 * | 11/1994 | Langdon et al. ...................... 428/137 |
| 5,368,910 * | 11/1994 | Langdon ............................... 428/137 |
| 5,382,245 | 1/1995 | Thompson et al. . |
| 5,429,629 * | 7/1995 | Latimer et al. ....................... 604/378 |
| 5,525,407 * | 7/1996 | Yang ................................... 428/218 |
| 5,643,653 * | 7/1997 | Griesbach, III et al. ............. 428/120 |
| 5,649,916 * | 7/1997 | DiPalma et al. ...................... 604/378 |
| 5,669,895 * | 9/1997 | Murakami et al. ................... 604/380 |
| 5,695,487 * | 12/1997 | Cohen et al. ......................... 604/384 |
| 5,700,254 * | 12/1997 | McDowall et al. ................... 604/378 |
| 5,797,894 * | 8/1998 | Delvaux ............................... 428/162 |

FOREIGN PATENT DOCUMENTS

| | | |
|---|---|---|
| 312 118 | 4/1989 | (EP) . |
| 391 814 | 10/1990 | (EP) . |
| 685 214 | 12/1995 | (EP) . |
| 686 384 | 12/1995 | (EP) . |
| 2 209 672 | 5/1989 | (GB) . |
| 90/14814 | 12/1990 | (WO) . |
| 93/09745 | 5/1993 | (WO) . |
| 96/00550 | 1/1996 | (WO) . |

* cited by examiner

*Primary Examiner*—John G. Weiss
*Assistant Examiner*—Carie Mager
(74) *Attorney, Agent, or Firm*—Burns, Doane, Swecker & Mathis, L.L.P.

(57) ABSTRACT

An absorbent article, such as a diaper, pant diaper, incontinence guard, sanitary napkin, wound dressing and the like, comprising a layer of continuous fibers, so-called tow, which have been bonded together in points, lines or spots in a bonding pattern (10), but otherwise are substantially unbonded to each other, and which layer comprises at least two zones (5a–e), as seen in the cross-sectional direction of the layer, which zones are different with respect to one or several properties such as basis weight, density, pore size, hydrophilicity/hydrophobicity and/or other absorption properties and/or properties affecting skin condition. Said layer can either be used as a liquid acquisition layer (5) in the article underneath a topsheet (2), as a topsheet (12), or as a combined topsheet and liquid acquisition layer (22).

38 Claims, 6 Drawing Sheets

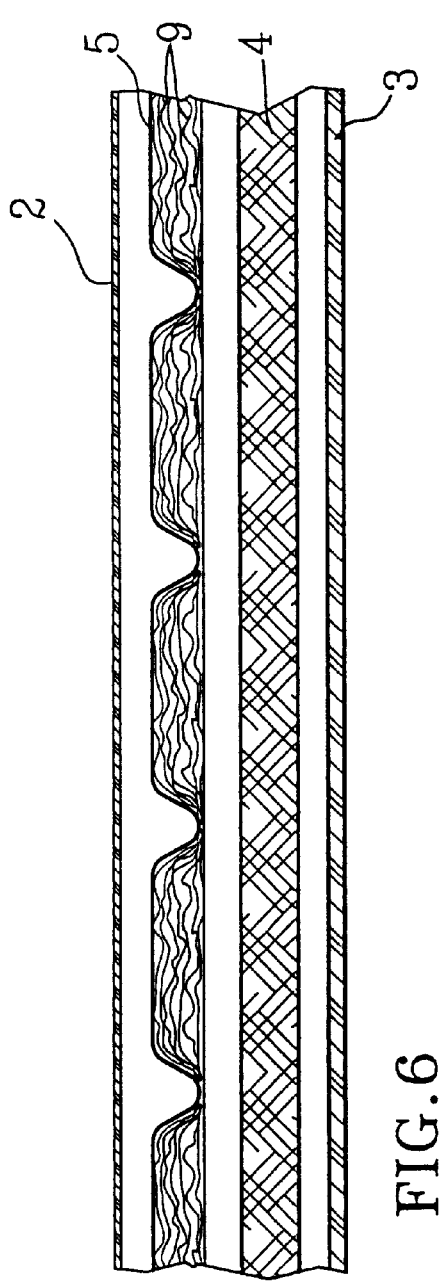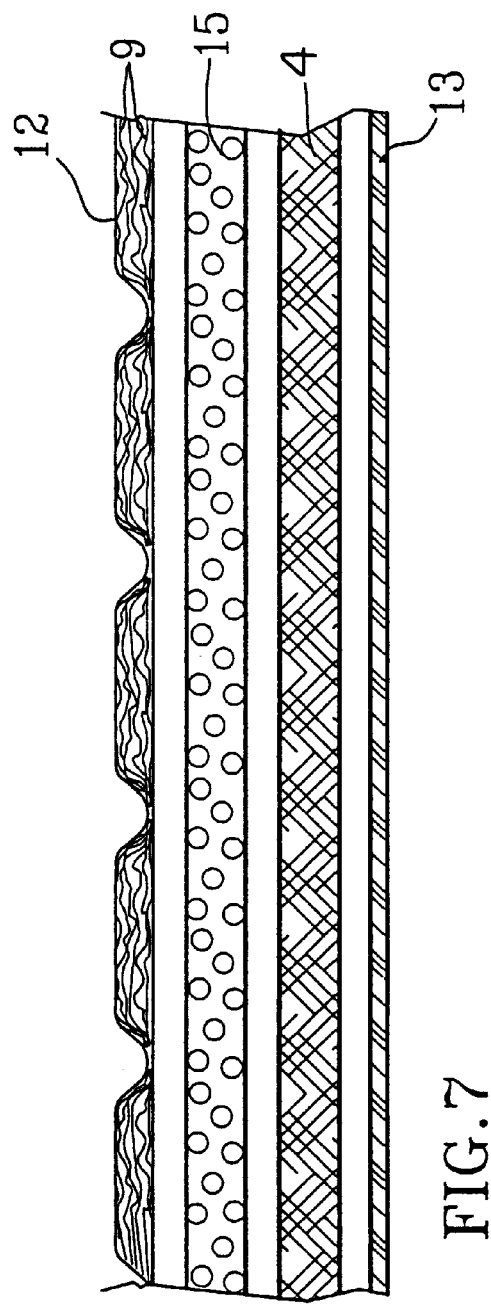

ABSORBENT ARTICLE

TECHNICAL FIELD

The present invention relates to an absorbent article, such as a diaper, pant diaper, incontinence guard, sanitary napkin, wound dressing and the like, of the kind comprising a liquid pervious topsheet, a liquid impervious backsheet and an absorbent body arranged therebetween.

BACKGROUND OF THE INVENTION

Absorbent articles of the above mentioned kind are intended for absorption of body fluids, such as urine and blood. As a liquid pervious topsheet which is facing the wearer during use, they usually exhibit a nonwoven material, for example of spunbond-type. It is also previously known to arrange a liquid acquisition layer between the topsheet layer and the absorbent body, said liquid acquisition layer having the ability to quickly receive large quantities of liquid, and to distribute the liquid and temporarily store it before it is absorbed by the underlying absorbent body. This is of great importance, especially in the thin compressed absorbent bodies of today, often comprising a high content of so called superabsorbents, which certainly have a high absorption capacity but in many cases a too low absorption rate in order to instantaneously be able to absorb the large quantity of liquid which can be discharged in a few seconds during urination. A porous, relatively thick acquisition layer, for example in the form of a fibrous wadding, a carded fibrous web, or another type of fibrous material, has a high instantaneous liquid-receiving capacity and is able to store the liquid temporarily until it has been absorbed by the absorbent body. The same applies for porous foam materials. The liquid is thereafter drained successively into the underlying absorbent body, after which the acquisition layer once again has the capacity to receive liquid from a repeated wetting.

Examples of absorbent articles comprising such porous acquisition layers are, for example, disclosed in U.S. Pat. No. 3,371,667, EP-A-0,312,118 and EP-A-0,474,777.

The materials used today as acquisition layers in absorbent articles are mostly functioning well, but are relatively expensive and can sometimes exhibit an insufficient acquisition rate, especially in the second and third wettings, if large quantities of liquid are involved.

It is previously known through EP-A-0,391,814 and GB-B-2,209,672 to use continuous, unbonded synthetic fibres, so-called tow, in absorbent articles for distributing liquid in the longitudinal direction of the article.

Another problem is that conventional liquid pervious topsheet materials used for absorbent articles of this kind, usually a nonwoven material of synthetic fibres, e.g. a spunbond material, often have a lower acquisition rate for liquid than the acquisition layer, wherein liquid can leak out from the article before it reaches the acquisition layer. This problem can of course be solved by using a topsheet material which is very open and therefore has a high liquid permeability. Such an open topsheet material may, however, cause problems with too low strength and sharp fibre ends from the acquisition layer which penetrate the open topsheet material and irritate the user.

OBJECT AND MOST IMPORTANT FEATURES OF THE INVENTION

The object of the present invention is to provide a material which exhibits a high acquisition rate for liquid also in repeated wettings, exhibits a high strength and wear resistance, high comfort, high processability and has a relatively low price. Furthermore, it should be possible to combine different wishes, concerning the function of the material and the absorption properties, in the same material. According to the invention, this has been achieved by means of a layer of continuous fibres, so-called tow, which are bonded in points, lines or spots in a bonding pattern, but otherwise are substantially unbonded to each other, and which layer comprises at least two different zones, as seen in the cross-sectional direction of the layer, which zones are different from each other with respect to one or several properties, such as basis weight, density, pore size, hydrophilicity/hydrophobicity and/or other absorption properties and/or properties affecting skin condition.

Herein, "cross-sectional direction of the layer" means a plane which is transverse to the fibre direction.

According to one embodiment, the layer exhibits different basis weight and/or density in its central portion than in its, in relation to the fibre direction, longitudinal edge portions, According to another embodiment, the layer comprises at least two different fibre types or fibre grades, which constitute said different zones. Thereby, the different fibre types can exhibit different thickness, fibre cross-section, crimp and/or elasticity modulus. Furthermore, they can be of different polymeric materials and/or exhibit different surface treatments.

The different fibre types can either constitute different layers in the z-direction of the layer, or different zones in the y-direction, or a combination of both.

The different fibre types can constitute different discreet zones in the article, or be partially integrated with each other.

The layer can be used as a liquid acquisition layer underneath a topsheet, as a topsheet material, or as an integrated topsheet/liquid acquisition layer.

Further features of the invention are evident from the following description and from the claims.

DESCRIPTION OF THE DRAWINGS

In the following, the invention will be described in greater detail with reference to embodiments shown in the accompanying drawings.

FIGS. 6–9 are schematic, exploded cross-sectional views in the longitudinal direction of four different embodiments of the article according to the invention.

DESCRIPTION OF EMBODIMENTS

Figure 1:
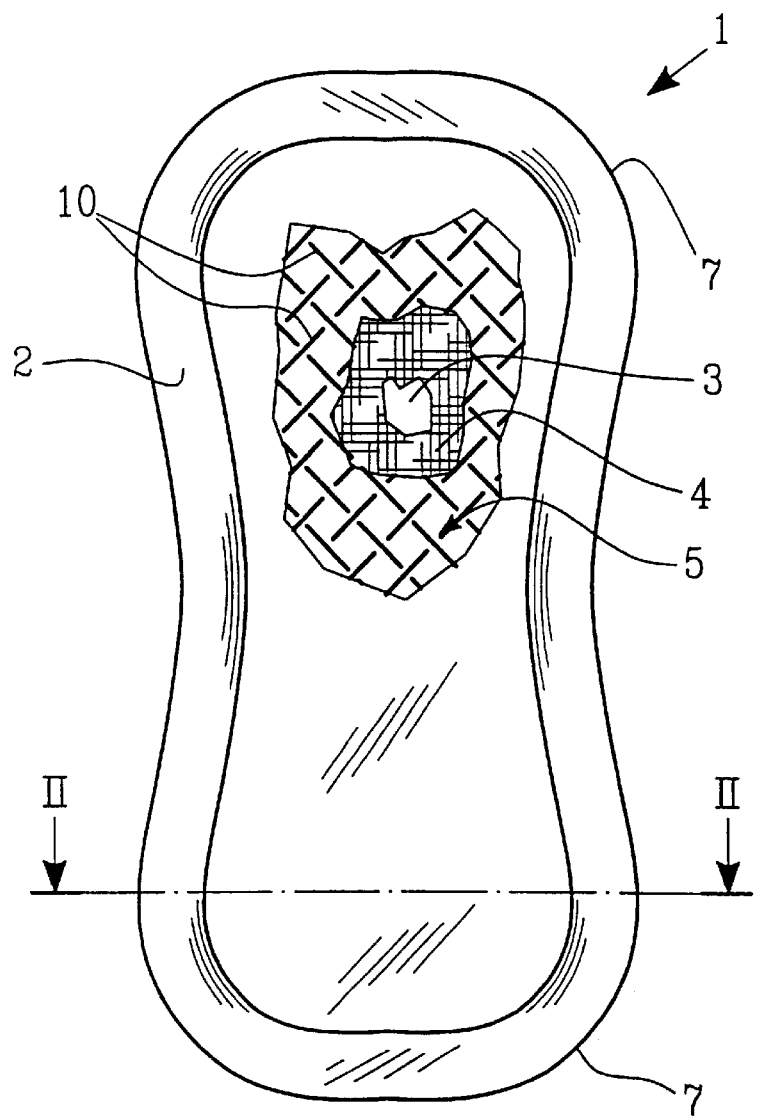
FIG. 1 is a plan view of an embodiment of an absorbent article according to the invention in the form of an incontinence guard.
Figure 2:
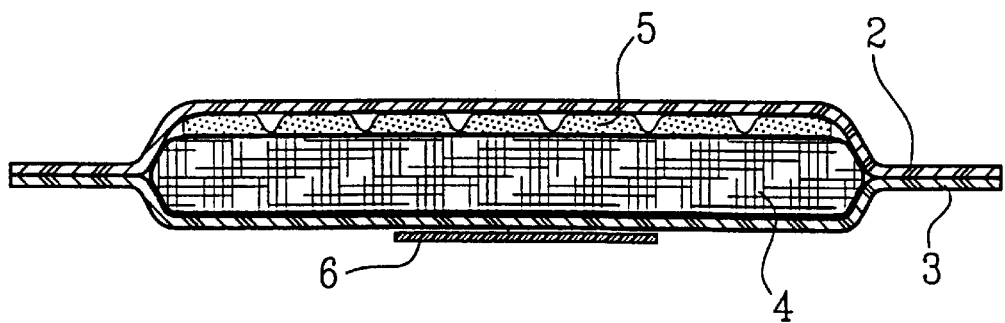
FIG. 2 is a section along the line II—II in FIG. 1.

In FIGS. 1 and 2, an embodiment of an incontinence guard 1 is shown, comprising a liquid pervious top layer 2, a liquid impervious back layer 3 and an absorbent body 4 enclosed therebetween. Furthermore, a porous and resilient liquid acquisition layer 5 is arranged between the liquid pervious top layer 2 and the absorbent body 4.

The liquid pervious top layer 2 can consist of a nonwoven material, for example a spunbond material of synthetic filaments, a meltblown material, a thermobonded material or a bonded carded fibrous material. The liquid impervious back layer 3 can consist of a plastic film, a nonwoven material coated with a liquid impervious material, or a hydrophobic nonwoven material which resists liquid penetration.

The top layer 2 and the back layer 3 have a slightly larger extension in the plane than the absorbent body 4 and the liquid acquisition layer 5, and extend outside the edges of these. The layers 2 and 3 are interconnected within the projecting portions, for example by means of gluing or welding with heat or ultrasonic.

The absorbent body 4 can be of any conventional type. Examples of commonly occurring absorption materials are cellulosic fluffpulp, tissue layers, highly absorbent polymers (so-called superabsorbents), absorbent foam materials, absorbent nonwoven materials, and the like. It is common to combine cellulosic fluff pulp with superabsorbents in an absorbent body. It is also common with absorbent bodies comprising layers of different materials with different properties when liquid acquisition capability, liquid distributing ability and liquid storage capacity are concerned. This is well-known to the person skilled in the art and therefore need not be described in detail. The thin absorbent cores, which are common in for example baby diapers and incontinence guards, often consist of a compressed, mixed or layered, structure of cellulosic fluff pulp and superabsorbent.

On the outside of the liquid impervious back layer 3, fastening means in the form of longitudinal strings 6 of a self-adhesive glue are arranged. Before use, the adhesive regions are suitably protected by a removable protective strip, not shown in the drawings, of paper or plastic film treated with a release agent. In the shown embodiment, the fastening means consist of longitudinal adhesive regions. A number of other adhesive patterns, e.g. transverse patterns, are of course conceivable, as well as other types of fastening means such as hook and loop surfaces, snap fasteners, frictional fixation, girdles, special underpants, or the like.

An incontinence guard of the type shown in FIG. 1 is primarily intended to be used by persons suffering from relatively light incontinence troubles and is easily accommodated inside a pair of ordinary underpants. Thereby, the fastening means 6 serve to keep the incontinence guard in its place inside the underpants during use.

The incontinence guard 1 is hourglass-shaped with wider end portions 7 and a narrower crotch portion 8 located between the end portions. The crotch portion 8 is the portion of the incontinence guard which during use is intended to be applied in the crotch region of the user and serve as a receiving area for the excreted body fluid.

Figure 3:
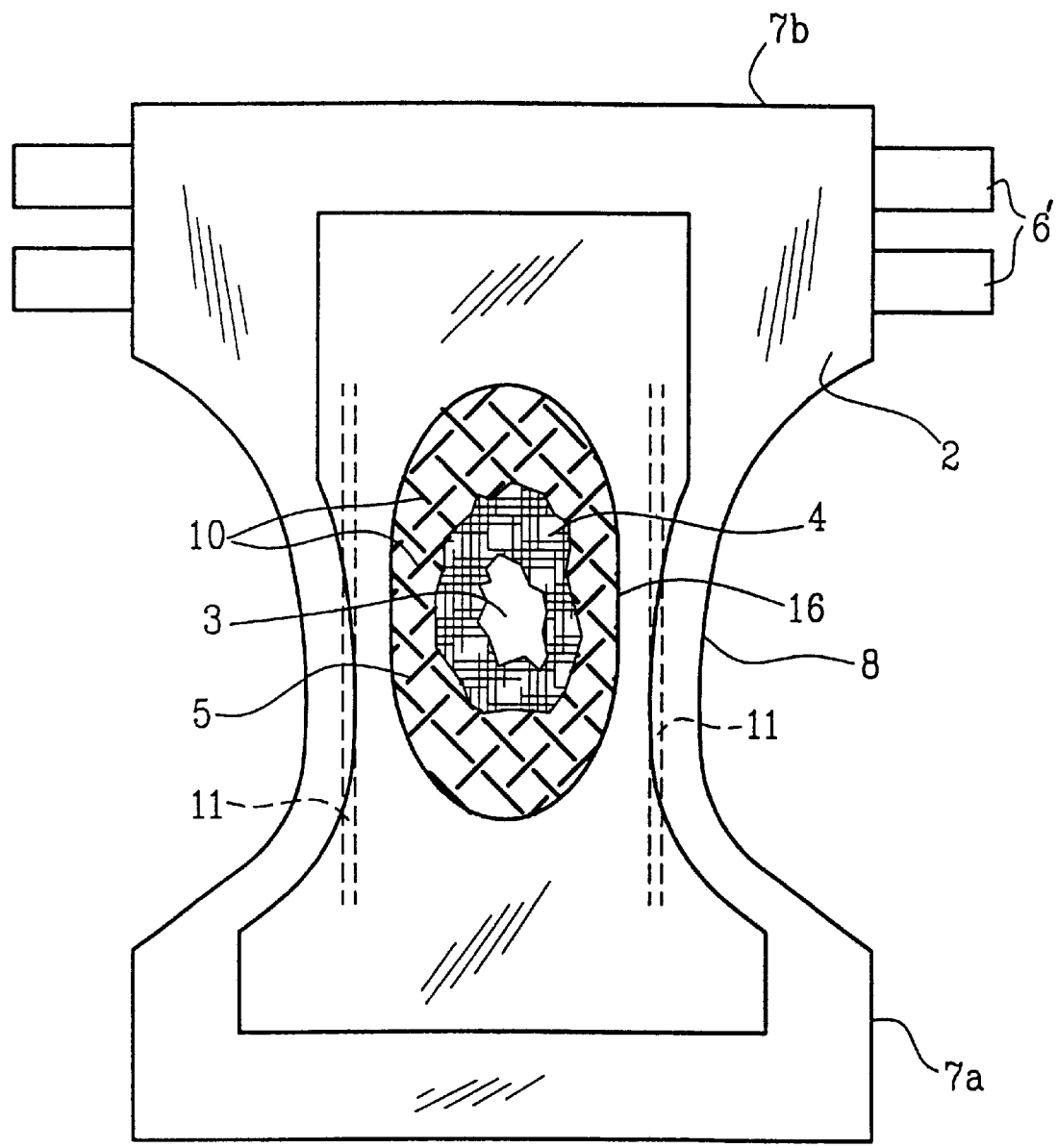
FIG. 3 shows, in plan view, an absorbent article in the form of a diaper.
Figure 4:
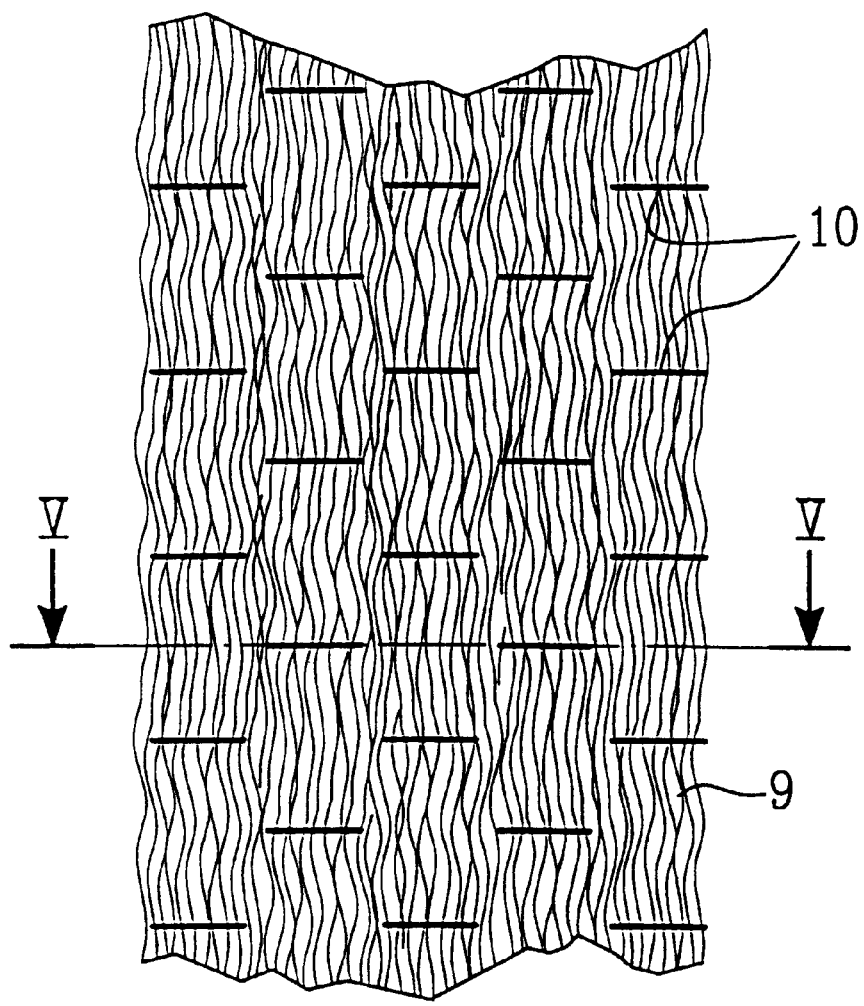
FIG. 4 schematically shows a portion of a fibrous layer according to the invention.
Figure 5:
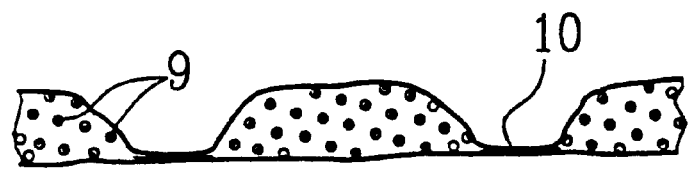
FIG. 5 shows, in magnification, a schematic section along the line IV—IV in FIG. 3.

In FIG. 3, there is shown an absorbent article in the form of a diaper, which like the above-described incontinence guard comprises a liquid pervious top layer 2, a liquid impervious back layer 3 and an absorbent body 4 enclosed therebetween, and further comprises an acquisition layer 5 applied between the top layer 2 and the absorbent body 4. In the shown embodiment, the top layer is provided with a hole 16, which is positioned in the intended wetting area, whereby the acquisition layer 5 is exposed directly towards the user in this area. Instead of one hole 16, several smaller holes may be provided. The absorbent also includes leg elastic threads 11 located on each side of the hole 16.

The diaper is intended to enclose the lower part of the trunk of the user as a pair of absorbent pants. It exhibits a front portion 7a intended to be facing forward on the user during use, a back portion 7b intended to be facing backwards on the user during use, and a narrower crotch portion 8, located between the front and the back portions, which is intended to be applied in the crotch region between the legs of the user. In order to enable the diaper to be put together in the desired pant shape, tape tabs 6' are arranged close to the rearwardly facing waist edge of the diaper, whereby the diaper 15 is kept together around the waist of the user. Other fastening means, such as hook and loop means, hooks, etc., are of course conceivable.

It should be noted that the incontinence guard and the diaper shown in the drawings and described above, only are two non-limiting examples of an absorbent article. Accordingly, the shape of the article, as well as its design otherwise, can be varied. The absorbent article can also be constituted of a pant diaper, a sanitary napkin, a wound dressing, or the like. The absorbent article can be either of a disposable or a reusable type. For products of reusable type, however, other materials than the above-described are relevant as a liquid pervious topsheet and as an absorbent body, respectively.

A porous and resilient acquisition layer 5, having the ability to quickly receive large amounts of liquid and to distribute the liquid and store it temporarily before it is absorbed by the underlying absorbent body 4, is arranged between the liquid pervious top layer 2 and the absorbent body 4. This ability should essentially be maintained also after wetting of the material. The acquisition layer 5 can cover either the entire absorbent body 4, extend outside it, or cover only the central portions of the absorbent body.

According to the invention, the acquisition layer consists of a layer 5 of continuous fibres 9, so-called tow, which have been bonded together in points, lines or spots of a bonding pattern 10, but otherwise are substantially unbonded to each other. In the embodiment shown in FIG. 1, the bonding pattern 10 is constituted of a line pattern with short lines arranged in a zigzag configuration. The bonding pattern is achieved by means of, for example, ultrasonic welding or other thermal bonding with simultaneous compression. Examples of other suitable thermal bonding methods are pattern calendering, laser bonding etc. A prerequisite for this is that at least some of the fibres in the tow are thermoplastic. Examples of thermoplastic fibres are polyolefines, polylactides, polyamides, polyester and the like. Also so-called bi-component fibres are included. As an alternative to thermal bonding, bonding can be achieved by means of a binding agent, using so-called printbonding or dot-bonding, or mechanically by means of so-called entanglement, using needling or water jets. The choice of bonding type is primarily decided by the type of fibres which are used in the tow.

The design of the bonding pattern 10 can of course vary within wide limits. The pattern can be in the form of points, spots or preferably lines. The lines can be straight, as well as curved, and the length can vary from a few millimetres, to the lines extending transversely or diagonally across the entire article. Preferably, the lines extend transversely or obliquely across the longitudinal direction of the fibres 9, so that a plurality of fibres are bonded to each other by each bonding line. It is also an advantage if different bonding lines overlap each other, as seen in the cross-direction of the article, so that a main part of the fibres are bonded at least along a part of their length.

The bonding pattern can be the same across the entire layer 5, or be different in different parts thereof.

Accordingly, the bonding pattern can be more sparse in the wetting area and be more dense outside the wetting area. It is also possible to design the bonding pattern in such a way that the layer 5 obtains different thickness in different portions of the article, for example thinner in the central portions and thicker in the surrounding edge portions in order to create a bowl-shape which provides a liquid receiving volume.

Fibre-tow is supplied in bags or in the form of bales or rolls of continuous fibres, which either are straight, crimped or curled. Crimped or curled fibres are preferred in this case, since they result in a very open and lofty structure. The bales or the like are opened in special converting devices, wherein the fibres are separated from each other, stretched and spread out into an essentially uniformly thick layer. The layer 5 is bonded in the desired bonding pattern, as described above, and is cut into suitable lengths. Alternatively, the bonding can take place after the cutting. Tow is a relatively cheap delivery form for fibres, in comparison with nonwoven, waddings, or the like, which normally are used as acquisition materials.

In Figs, 4 and 5, a portion of a layer 5 of fibre-tow, which has been bonded in a simple bonding pattern 10 with transverse, short lines. The fibres 9 are unbonded to each other, except at the bonding points.

The fibres in the tow can be of any suitable material, such as polyethylene, polypropylene, polyamide, polyester, polylactide, polyvinyl acetate, cellulose acetate, regenerated cellulosic fibres such as viscose and rayon, or of bi-component type with a shell of a polymer having a lower melting point and a core of a polymer having a higher melting point. Fibres which exhibit a high resiliency, for example polyester, co-polyester and polypropylene, are particularly preferred.

The fibre thickness may vary, but is suitably within the interval 0.5–50 dtex, preferably 1.5–25, and most preferably 2–15 dtex, if the material is to be used as an acquisition material. The open, lofty structure in combination with the relatively coarse fibre dimension provides a very rapid liquid acquisition. In addition, the material is strong due to the longitudinal continuous fibres, which provide strength in the longitudinal direction, and the bonding pattern, which provides strength in the transverse direction.

In the above-disclosed example, the material layer 5 has been used as an acquisition layer 5 underneath a liquid pervious top layer 2. This is also shown in FIG. 6. In this case, the basis weight of the bonded fibre-tow should be within the interval 10–200 g/m$^2$, preferably 30–150, and most preferably 30–100 g/m$^2$. The top layer 2 can be of any optional type, but preferably exhibits a relatively open structure which permits a rapid liquid acquisition. The top layer 2 may be bonded to the acquisition layer 5 in bonding points 10.

In FIG. 7, an alternative embodiment is shown, wherein the material layer 5 according to the invention has been used as a liquid pervious top layer 12. In this case, the basis weight should be within the interval 5–200 g/m$^2$, preferably 5–50 g/m$^2$ and the fibre thickness within the interval 0.5–50 dtex, preferably 1.5–25, and most preferably 2–15 dtex. In other respects, the material can be the same as described above. Underneath the material layer 5, applied as a top layer, an acquisition layer 15 which can be of any optional type is arranged. The absorbent article according to FIG. 7 further comprises an absorbent body 4 and a liquid impervious back layer 13.

Figure 8:
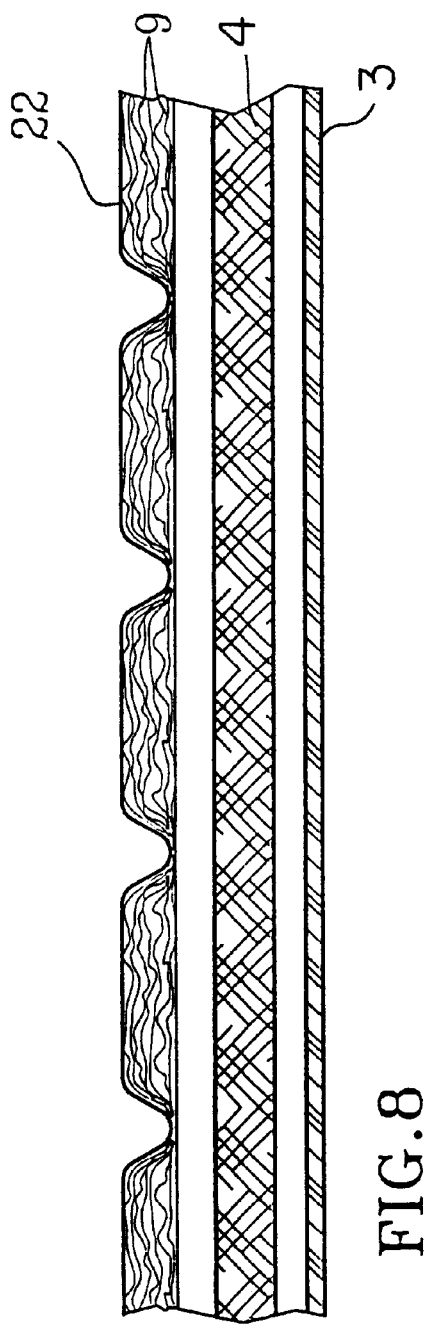

In the embodiment according to FIG. 8, the material layer 5 according to the invention has been used as a combined top layer and acquisition layer 22. In this case, the basis weight should be within the interval 10–200 g/m$^2$, preferably 30–150, and most preferably 30–100 g/m$^2$, and the fibre thickness within the interval 0.5–50 dtex, preferably 1.5–25, and most preferably 2–15 dtex. In a conventional way, the absorbent article according to FIG. 8 further comprises an absorbent body 4 and a liquid impervious back layer 3.

Figure 9:
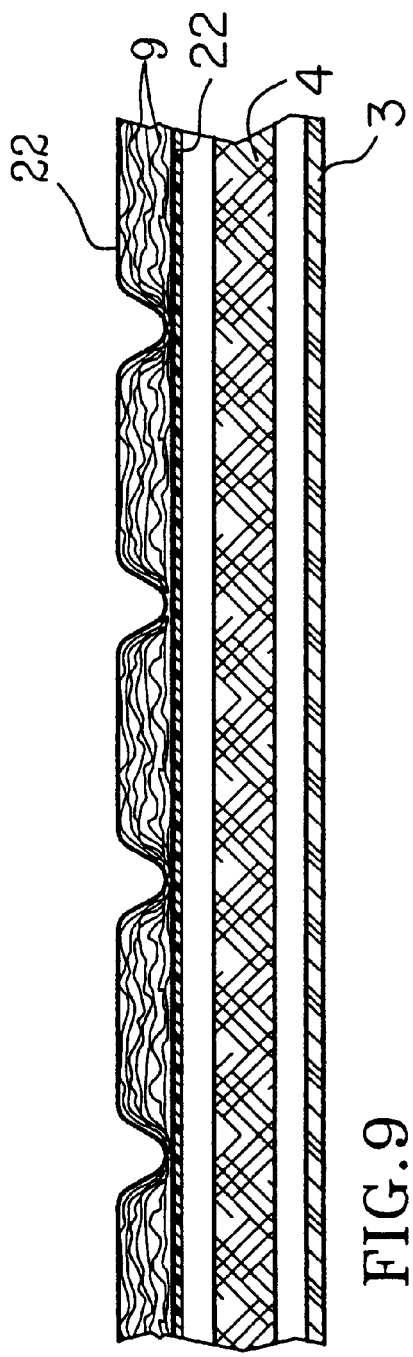

The embodiment according to FIG. 9 differs from what is shown in FIG. 8 by the fact that a carrier material 22, e.g. in the form of a nonwoven, has been integrated on the underside of the combined top layer/acquisition layer 5. Such a carrier material can of course, alternatively or also, be integrated with the upper side of the layer 5 or with the layer 5 according to FIG. 6 or FIG. 7.

In the embodiments according to FIGS. 7–9, the bonded fibre-tow according to the invention will be directly contacting the skin of the wearer. In this case, extraordinary high demands are made on the comfort and softness of the material. Since the material consists of continuous fibres, there are no sharp fibre ends which protrude and may irritate the skin, but the material is very soft and pliable. In addition, it exhibits a sufficient strength and wear resistance due to the longitudinal continuous fibres 9, which provide strength in the longitudinal direction, and the bonding pattern, which provides strength in the transverse direction. In case part of the bonding pattern would break, the remaining parts of the pattern still exist.

As mentioned above, it is particularly advantageous if crimped or curled fibres are used in the tow, since they provide a particularly open and lofty structure. It is also possible to use a combination of straight and crimped or curled fibres.

It is also possible to use different fibre types or different fibre thicknesses in different portions of the material, i.e. in different layers or zones thereof. This in order to create the desired absorption pattern. In this way, gradients of different hydrophilicity and pore size can be created. This will be described in greater detail below, with reference to FIGS. 10 and 11. An admixture of superabsorbent fibres into the tow is also conceivable.

By means of utilizing tow when manufacturing the material according to the invention, it is easy from a processability point of view to create zones 5a–e, as seen in the cross-sectional direction of the material, which are different with respect to one or several properties such as basis weight, density, pore size, hydrophilicity/hydrophobicity and/or other absorption-influencing properties. The feeding of the material to the bonding station, where the bonding of the fibres in a desired bonding pattern takes place, can for example be done in such a way that more fibres are fed in along the edges, or alternatively along the central portion, whereby different basis weights are obtained in the edge portions and in the central portion, 5a,c and 5b, respectively. Varying basis weight can also be created by means of folding the opened and spread-out fibre-tow in the longitudinal direction in a suitable way before feeding it into the bonding station. Another method is to combine two or several tow webs into one web by means of placing the different webs on top of each other, overlapping in such a way that different basis weights are created in different portions.

A higher density in different portions of the layer 5 can be created by means of compressing this non-uniformly across the y-direction.

The layer 5 can also contain at least two different types of fibres 9, which constitute the different zones 5a–e. Thereby, the different types of fibres 9 can exhibit different thickness, fibre cross-section, crimp and/or elasticity modulus. They may, furthermore or alternatively, be of different polymeric materials and/or exhibit different surface treatments, wherein they for example can have different hydrophilicity/hydrophobicity.

Figure 10:
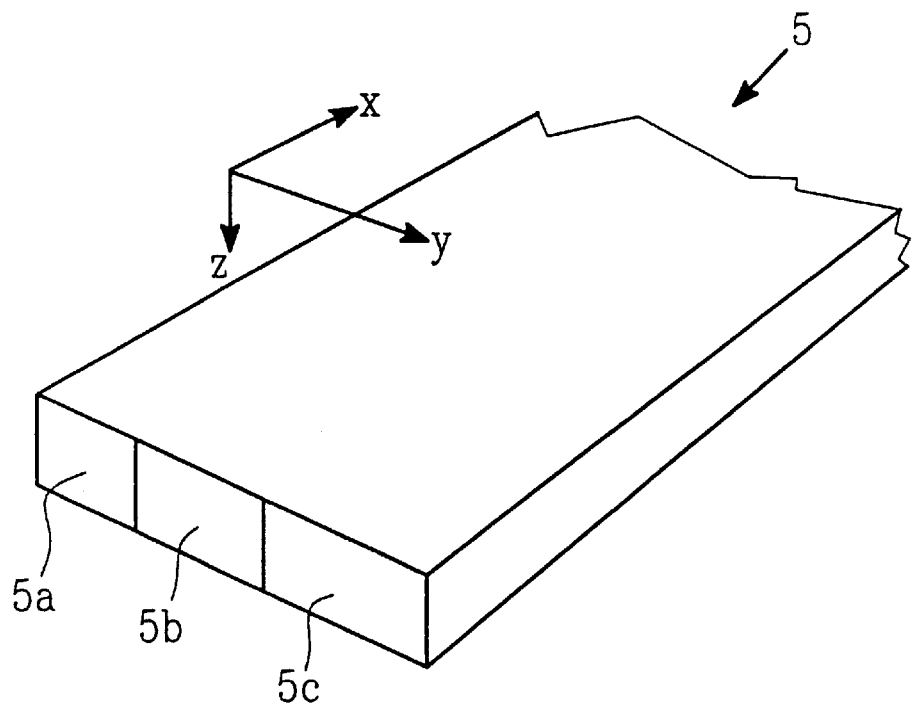
FIGS. 10 and 11 show schematic, cross-sections through fibre layers according to the invention with varying properties across the cross-section.
Figure 11:
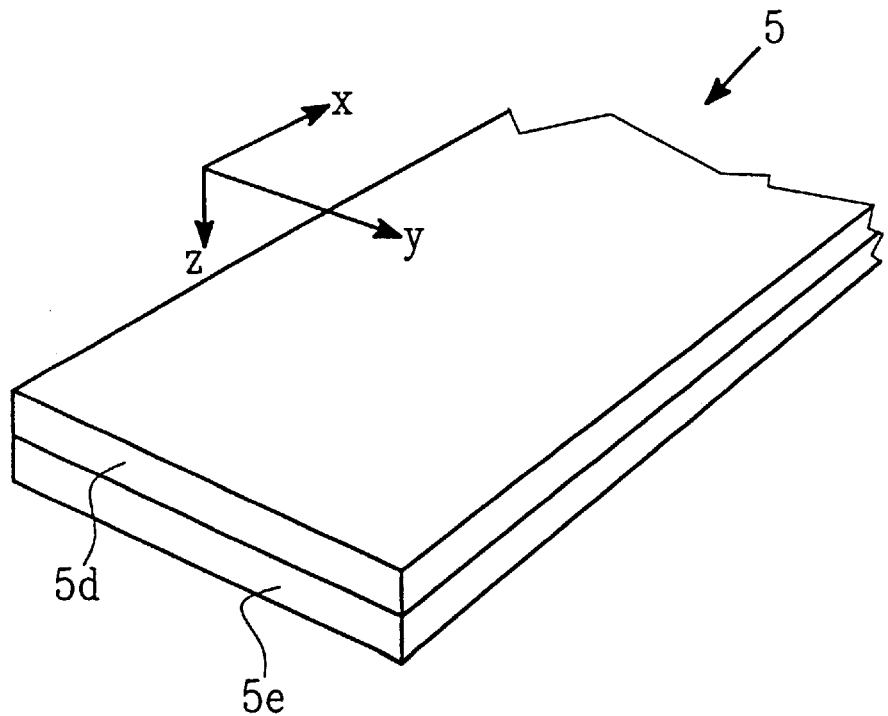

The different fibre types may either constitute different layers 5d,e in the z-direction of the layer 5 (FIG. 11) or constitute different zones 5a–c in the y-direction of the layer 9 (FIG. 10). A combination of these two alternatives is of course also possible, for example by means of the upper layer 5d in its turn being divided into different zones in the y-direction. The different fibre types may either form substantially discreet zones, or be partially integrated with each other.

Herein, the "x-direction" of the layer 5 means the direction in which the continuous fibres 9 extend, whereas the "y-direction" means the direction substantially transverse to the fibre-direction. The "z-direction" means the thickness-direction of the layer. The layer 5 can of course be arranged in the article either in the longitudinal direction or in the transverse direction of the article, i.e. the continuos fibres 9 in the layer 5 either extend in the longitudinal or in the transverse direction of the article.

The manufacture of a layer with different fibre types in different zones can easily be accomplished by means of fibre-tow of the different fibre types being opened, being spread-out and combined into a mutual fibre web which thereafter is bonded in the desired bonding pattern.

By means of utilizing fibres with different thickness in the different zones, the layer obtains different absorption and distributing properties in the different zones. Accordingly, fibres of a higher thickness can be used in an upper layer 5d and thinner fibres in the lower layer 5e, whereby a pore size gradient is created in the z-direction of the layer which facilitates the liquid transport in the z-direction. It is also possible that the central zone 5b of the layer consists of thicker fibres than in the edge portions 5a,c, in order to create a rapid liquid acquisition in the central zone 5b.

By means of utilizing fibres with differently-shaped fibre cross-sections in the different zones, pore size differences or other differences in distributing ability between the different zones can also be created. This is also the case when utilizing different crimp degrees of the fibres in the different zones.

Fibres of different polymer types, as well as with different surface treatments, result in different hydrophilicity/hydrophobicity properties. For instance, hydrophilic fibres can be used in the central zone 5b and hydrophobic fibres in the edge portions 5a and c, in order to create side barriers against liquid spreading out towards the edges. It is also conceivable to create several narrow longitudinal, hydrophobic streaks of hydrophobic fibres in an otherwise hydrophilic layer. These hydrophobic streaks create lateral micro-barriers.

Furthermore, they provide a better surface dryness. If the continuous fibres 9 in the layer 5 are positioned in the transverse direction of the absorbent article, streaks can be created in the transverse direction of the article in a corresponding way.

In a corresponding way, narrow streaks can be formed in the longitudinal or transverse direction of the article by means of fibres which have been treated with for example a skin-friendly lotion, smell-inhibitor, bactericides, fungicides or another substance affecting the skin condition. Examples of such substances are zeolites, active carbon, aloe vera, metal salts, organic acids or salts thereof, and other substances known and used for these purposes.

It is also possible to create a hydrophilicity gradient in the z-direction of the layer 5 by means of arranging fibres with increasing hydrophilicity from the upper 5d towards the lower layer 5e.

The invention is of course not limited to what has been disclosed above or has been shown in the drawings, but a plurality of variations are conceivable within the scope of the claims. Accordingly, the number of zones in the y- or z-direction can of course vary from two and upwards. The zones can also consist of a mixture of, for example, hydrophilic/hydrophobic fibres, straight/crimped fibres, thick/thin fibres, etc. However, there should be at least two zones which are different in some of the above-mentioned respects.

What is claimed is:

1. An absorbent article, such as a diaper, pant diaper, incontinence guard, sanitary napkin, or wound dressing, the absorbent article comprising:
    a liquid pervious layer of continuous tow fibres which have been bonded together in points, lines or spots in a non-random bonding pattern, but otherwise are substantially unbonded to each other, and the layer of continuous fibres comprises at least two zones, as seen in a cross-sectional direction of the layer of continuous fibres, which zones are different with respect to pore size;
    a liquid impervious back layer, and
    an absorbent body arranged therebetween.

2. The absorbent article according to claim 1, wherein the layer of continuous fibres exhibits a basis weight between 5–200 g/m$^2$.

3. The absorbent article according to claim 1, wherein the layer of continuous fibers exhibits a basis weight between 5–50 g/m$^2$.

4. An absorbent article, such as a diaper, pant diaper, incontinence guard, sanitary napkin, or wound dressing, the absorbent article comprising:
    a liquid pervious top layer,
    a liquid impervious back layer,
    an absorbent body arranged therebetween, and
    a layer of continuous tow fibres, which are bonded together in points, lines or spots in a non-random bonding pattern, but otherwise are substantially unbonded to each other, and the layer of continuous fibres comprises at least two zones, as seen in a cross-sectional direction of the layerof continuous fibres, which zones are different with respect to at least one property selected from the group consisting of basis weight, density, pore size, hydrophilicity, hydrophobicity, fibre thickness, fibre cross section, fibre crimp, fibre elastic modulus, fibre surface treatment, and fibre material.

5. The absorbent article according to claim 4, wherein the layer of continuous fibres has a different basis weight in its central portion than in its edge portions.

6. The absorbent article according to claim 4, wherein each of said zones of the layer of continuous fibres contains a different type of fiber.

7. The absorbent article according to claim 4, wherein different types of fibres have different thickness, fibre cross-section, crimp or elasticity modulus.

8. The absorbent article according to claim 6, wherein the different types of fibres are of different polymeric materials or exhibit different surface treatments.

9. The absorbent article according to claim 6, wherein the different fibre types constitute different layers in a first direction of the layer of continuous fibres.

10. The absorbent article according to claim 6, wherein the different fibre types constitute different zones in a second direction of the layer of continuous fibres.

11. The absorbent article according to claim 6, wherein the different fibre types constitute different discrete zones in the layer of continuous fires.

12. The absorbent article according to claim 6, wherein the different fibre types are partially integrated with each other.

13. The absorbent article according to claim 1, wherein the layer of continuous fibres is utilized as a liquid acquisition layer applied between the top layer and the absorbent body.

14. The absorbent article according to claim 13, wherein the layer of continuous fibres exhibits a basis weight between 10–200 g/m$^2$.

15. The absorbent article according to claim 13, wherein the top layer includes at least one hole, in the intended wetting area of the article, through which hole the liquid acquisition layer is exposed towards a user.

16. The absorbent article according to claim 13, wherein the layer of continuous fibers exhibits a basis weight between 30 to 150 g/m$^2$.

17. The absorbent article according to claim 13, wherein the layer of continuous fibers exhibits a basis weight about 30 to 100 g/m$^2$.

18. The absorbent article according to claim 4, wherein at least a part of the continuous fibres in said layer are crimped or curled.

19. The absorbent article according to claim 4, wherein the bonding pattern comprises dots, spots or lines which cross a longitudinal direction of the continuous fibres.

20. The absorbent article according to claim 19, wherein different bonding lines over-lap each other, as seen in a cross-direction of the article, so that a main part of the fibres are bonded at least along a part of their length.

21. The absorbent article according claim 4, wherein the layer of continuous fibres is utilized as an integrated topsheet/liquid acquisition layer.

22. The absorbent article according to claim 21, wherein the layer of continuous fibres exhibits a basis weight between 10–200 g/m$^2$.

23. The absorbent article according to claim 21, wherein the layer of continuous fibers exhibits a basis weight between 30–150 g/m$^2$.

24. The absorbent article according to claim 21, wherein the layer of continuous fibers exhibits a basis weight between 30–100 g/m$^2$.

25. The absorbent article according to claim 4, further comprising a carrier material for supporting the layer of continuous fibres.

26. The absorbent article according to claim 25, wherein the carrier material is a nonwoven material.

27. The absorbent article according to claim 4, wherein the zones are different with respect to basis weight.

28. The absorbent article according to claim 4, wherein the zones are different with respect to density.

29. The absorbent article according to claim 4, wherein the zones are different with respect to pore size.

30. The absorbent article according to claim 4, wherein the zones are different with respect to hydrophilicity.

31. The absorbent article according to claim 4, wherein the zones are different with respect to hydrophobicity.

32. The absorbent article according to claim 4, wherein the zones are different with respect to fibre thickness.

33. The absorbent article according to claim 4, wherein the zones are different with respect to fibre cross-section.

34. The absorbent article according to claim 4, wherein the zones are different with respect to fibre crimp.

35. The absorbent article according to claim 4, wherein the zones are different with respect to fibre elastic modulus.

36. The absorbent article according to claim 4, wherein the zones are different with respect to fibre surface treatment.

37. The absorbent article according to claim 4, wherein the zones are different with respect to fibre material.

38. The absorbent article according to claim 4, wherein the layer of continuous fibres has a different density in its central portion than in its edge portions.

* * * * *